United States Patent [19]

Mühlebach et al.

[11] Patent Number: 5,391,681

[45] Date of Patent: Feb. 21, 1995

[54] CURABLE COMPOSITIONS BASED ON EPOXY RESINS OR MIXTURES OF EPOXY RESINS AND POLYISOCYANATES CONTAINING TRISIMIDAZOLYL TRIAZINES

[75] Inventors: Andreas Mühlebach, Belfaux; Peter Flury, Himmelried, both of Switzerland

[73] Assignee: Ciba-Geigy Corporation, Ardsley, N.Y.

[21] Appl. No.: 68,376

[22] Filed: May 27, 1993

[30] Foreign Application Priority Data

Jun. 5, 1992 [CH] Switzerland .................. 1810/92

[51] Int. Cl.$^6$ .............. C08G 18/20; C08G 59/00; C08G 59/68; C08L 63/00; C08L 75/00; C08K 5/29; C08K 5/3445; C08K 5/3492

[52] U.S. Cl. ........................... 528/45; 252/182.2; 252/182.23; 252/182.24; 252/182.27; 252/182.31; 502/159; 502/200; 523/461; 524/720; 524/871; 525/403; 525/523; 525/528; 528/49; 528/53; 528/54; 528/73; 528/94; 528/117; 528/118; 528/123; 528/407; 528/408; 528/418; 528/421

[58] Field of Search ............ 528/45, 53, 54, 94, 528/117, 123, 407, 408, 418, 421, 49, 73, 118; 525/523, 528, 403; 502/159, 200; 252/182.2, 182.23, 182.24, 182.27, 182.31; 523/461; 524/720, 871

[56] References Cited

U.S. PATENT DOCUMENTS

| | | | |
|---|---|---|---|
| 3,155,628 | 11/1964 | Bloomfield | 525/523 |
| 3,268,474 | 8/1966 | Hardy et al. | 523/461 |
| 3,308,122 | 3/1967 | Tolkmith | 544/198 |
| 3,366,601 | 1/1968 | Cragar et al. | 528/107 |
| 3,563,988 | 2/1971 | Feichtinger et al. | 528/407 |
| 3,631,150 | 12/1971 | Green | 528/407 |
| 3,839,282 | 10/1974 | Sweeny et al. | 525/523 |
| 4,205,156 | 5/1980 | Sawa et al. | 528/118 |
| 4,246,394 | 1/1981 | Schülde et al. | 528/94 |
| 4,511,596 | 4/1985 | Berner | 427/44 |
| 4,533,715 | 8/1985 | Lee et al. | 528/73 |
| 4,708,984 | 11/1987 | Forgione et al. | 528/528 |
| 4,710,542 | 12/1987 | Forgione et al. | 525/528 |
| 4,976,837 | 12/1990 | Hughes et al. | 204/181.7 |
| 5,175,219 | 12/1992 | Burba et al. | 525/523 |
| 5,175,220 | 12/1992 | Burba et al. | 525/523 |
| 5,210,169 | 5/1993 | Mühlebach et al. | 528/45 |

FOREIGN PATENT DOCUMENTS

| | | |
|---|---|---|
| 0050939 | 5/1982 | European Pat. Off. . |
| 0114784 | 8/1984 | European Pat. Off. . |
| 0500495 | 8/1992 | European Pat. Off. . |
| 1720526 | 8/1984 | Germany . |

OTHER PUBLICATIONS

Chemical Abstract 91:125037c (Oct.-1979).
Derwent Abstract No.: 78-34424A (Mar.-1978).
Derwent Abstract 85-150653/25 of Japanese patent J6-0084-283-A (Mar 13, 1985).
Derwent Abstract 84-314854/51 of Japanese patent J5-9196-377-A (Nov. 7, 1984).
Chemical Abstract vol. 102:167944x (1985).

*Primary Examiner*—John Kight, III
*Assistant Examiner*—Rabon Sergent
*Attorney, Agent, or Firm*—William A. Teoli, Jr.

[57] ABSTRACT

Curable compositions based on epoxy resins or a mixture of epoxy resins and polyisocyanates and containing at least one compound of formula I:

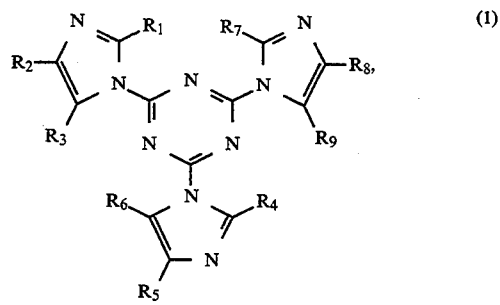

(I)

wherein $R_1$, $R_2$, $R_3$, $R_4$, $R_5$, $R_6$, $R_7$, $R_8$ and $R_9$ are each independently of one another hydrogen, alkyl, aryl, arylalkyl or halogen, and $R_2$ together with $R_3$ and $R_5$ together with $R_6$ and $R_8$ together with $R_9$ may each also represent a fused benzene ring.

The compositions have high reactivity and at the same time good storage stability.

11 Claims, No Drawings

CURABLE COMPOSITIONS BASED ON EPOXY RESINS OR MIXTURES OF EPOXY RESINS AND POLYISOCYANATES CONTAINING TRISIMIDAZOLYL TRIAZINES

The present invention relates to curable compositions based on epoxy resins or mixtures of epoxy resins and polyisocyanates, to a process for curing said resins or resin mixtures, and to the products obtainable with said compositions.

It is common practice to use different compounds as curing agents and/or curing accelerators for compositions of the above kind, typically dicyandiamide, chlorotoluron or imidazole and imidazole derivatives.

It is already known to use substituted triazines for these purposes. Thus JP Kokai 60/84 283 (1985) discloses the use of 2,4-diamino-6-[2-(2-phenyl-1H-imidazol1-yl)ethyl]triazine as hardener for polyepoxide resins, and JP Kokai 59/196 377 (1984) discloses curable compositions based on epoxy resins, butadiene copolymers and bisphenol, and additionally containing 2,4-diamino-6-[2-(2-methyl-1H-imidazol-1-yl)ethyl]triazine and dicyandiamide, and the use thereof as structural adhesives.

All the aforementioned compositions, however, are not entirely satisfactory. For example, they are insufficiently reactive at 100°–110° C. or else are sufficiently reactive but have an inadequate shelf-life. Other important properties of many prior art compositions are unsatisfactory, for example the curing rate, i.e. the degree of cure attainable in a specific period of time and at a specific temperature, and, in particular, the adhesive and bonding strength of the cured material.

The present invention has for its object to provide a curable composition based on epoxy resins or mixtures of epoxy resins and polyisocyanates, which composition has good reactivity even in the temperature range of 100°–110° C. and still has good storage stability.

This object is achieved by using curable compositions based on epoxy resins or mixtures of epoxy resins and polyisocyanates and containing at least one compound of formula I:

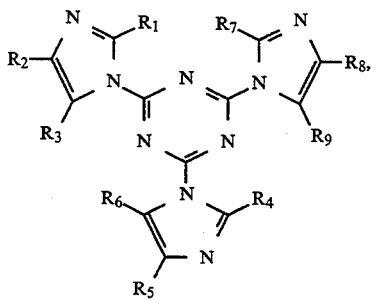

(1)

wherein $R_1$, $R_2$, $R_3$, $R_4$, $R_5$, $R_6$, $R_7$, $R_8$ and $R_9$ are each independently of one another hydrogen, alkyl, aryl, arylalkyl, or halogen, and $R_2$ together with $R_3$ and $R_5$ together with $R_6$ and $R_8$ together with $R_9$ may each also represent a fused benzene ring.

It has been found that the use of compounds of formula I above as hardeners or co-hardeners or accelerators in compositions based on epoxy resins or mixtures of epoxy resins and polyisocyanates result in good reactivity, especially at low temperatures, and at the same time in good storage stability of the compositions. The novel compositions also have a particularly good stability/reactivity ratio, although these two properties are normally in opposition to each other. To achieve a long shelf-life it is advantageous to use as weakly reactive a crosslinking or curing agent as possible. However, weakly reactive curing agents result in lengthy gel times, especially at low temperature. Furthermore, the compositions of this invention, when cured under the same conditions, exhibit an enhanced degree of cure. Coatings of novel compositions exhibit after cure a better bond strength than prior art compositions. This is especially advantageous for their utility as adhesives.

$R_1$ to $R_9$ as "alkyl" in formula 1 are preferably unbranched or branched alkyl of 1 to 10 carbon atoms which may also carry one or more than one substituent, typically hydroxyl, halogen or $C_1$–$C_4$alkoxy groups. Illustrative examples of such groups are methyl, ethyl, propyl, isopropyl, n-butyl, tert-butyl, octyl and 2-hydroxyethyl. The particularly preferred meaning of alkyl is $C_1$–$C_4$alkyl. $R_1$ to $R_9$ as "aryl" are preferably aryl groups which contain 5 to 10 ring carbon atoms and may also be substituted, typically by halogen atoms or $C_1$–$C_4$alkyl or $C_1$–$C_4$alkoxy groups, and which may also contain hetero atoms such as nitrogen, oxygen or sulfur. Aryl in this case is preferably phenyl and substitued phenyl. $R_1$ to $R_9$ as "arylalkyl" are preferably $C_1$–$C_4$alkyl which carries aryl substituents, preferably those defined above in connection with "aryl", and preferably carries 1 or 2 such substituents. The preferred arylalkyl radical is benzyl. $R_1$ to $R_9$ as "halogen" are preferably chloro or bromo. Where $R_2$ together with $R_3$ or $R_5$ together with $R_6$ or $R_8$ together with $R_9$ represent a fused benzene ring, the imidazole derivative is benzimidazole. This derivative too may also carry substituents, typically one or more than one halogen atom or $C_1$–$C_4$alkyl or $C_1$–$C_4$alkoxy group.

Particularly preferred compositions of this invention containing compounds of formula 1 are those wherein $R_1$ to $R_9$ are each independently of one another hydrogen, alkyl, preferably $C_1$–$C_4$alkyl, or aryl, preferably phenyl.

Some of the compounds of formula 1 are already known. They may conveniently be prepared in general accordance with the process disclosed in US-A-3 308 122 by reacting cyanuric chloride in an inert solvent such as tetrahydrofuran, diethyl ether, toluene, xylene or cyclohexane, and in the presence of a proton acceptor, typically a non-nucleophilic organic base such as triethylamine, with about a stoichiometric amount of a suitably substituted imidazole or benzimidazole derivative. The imidazole or benzimidazole derivatives required for the reaction are also themselves suitable proton acceptors, in which case they must naturally be used in excess. The starting imidazole can be easily recovered by neutralising the imidazolium solution initially with a strong base and then with a suitable solvent, conveniently one of those named above.

Substituted imidazoles suitable for use in the practice of this invention can be obtained in conventional manner, i.e. by the Radziszewski reaction, in accordance with the following reaction equation (exemplifying the imidazole of formula 1 containing $R_1$, $R_2$ and $R_3$):

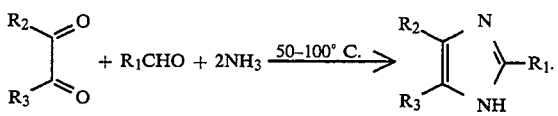

Many imidazole derivatives are also commercially available. Especially preferred imidazoles on account of their wide distribution and availability are imidazole, 2-methylimidazole, 4(5)-methylimidazole, 2-ethylimidazole, 2-isopropylimidazole, 2-ethyl-4(5)-methylimidazole, 2-phenylimidazole and 2-benzylimidazole.

Also preferred are compositions containing compounds of formula 1, wherein $R_1$, $R_4$ and $R_7$ as well as $R_2$, $R_5$ and $R_8$ and $R_3$, $R_6$ and $R_9$ are identical. Because of its relatively weak reactivity, however, tris(benzimidazol-1-yl)triazine is excluded. These compounds are ordinarily solids with melting points above 100° C. and are of particularly sparing solubility. This property facilitates not only the preparation of the compounds, but also enhances the shelf-life of the corresponding compositions.

All customary di-and polyepoxides and epoxy resin prepolymers are suitable epoxy resins for the practice of this invention. The di- and polyepoxides may be aliphatic, cycloaliphatic or aromatic compounds. Typical examples of such compounds are the glycidyl ethers and β-methylglycidyl ethers of aliphatic or cycloaliphatic diols or polyols, including those of ethylene glycol, 1,2-propanediol, 1,3-propanediol, 1,4-butanediol, diethylene glycol, polyethylene glycol, polypropylene glycol, glycerol, trimethylolpropane or 1,4-dimethylolcyclohexane or of 2,2-bis(4-hydroxycyclohexyl)propane, the glycidyl ethers of di- and polyphenols, typically resorcinol, 4,4'-dihydroxydiphenylmethane, 4,4'-dihydroxydiphenyl-2,2-propane, novolaks and 1,1,2,2-tetrakis(4-hydroxyphenyl)ethane. Further examples are N-glycidyl compounds, including diglycidyl compounds of ethylene urea, 1,3-propylene urea or 5-dimethylhydantoin or of 4,4'-methylene-5,5'-tetramethyl-dihydantoin, or those such as triglycidyl isocyanurate.

Further glycidyl compounds of technical importance are the glycidyl esters of carboxylic acids, especially di-and polycarboxylic acids. Typical examples are the glycidyl esters of succinic acid, adipic acid, azelaic acid, sebacic acid, phthalic acid, terephthalic acid, tetraand hexahydrophthalic acid, isophthalic acid or trimellitic acid or of dimerised fatty acids.

Exemplary of polyepoxides that differ from glycidyl compounds are the diepoxides of vinylcyclohexene and dicyclopentadiene, 3-(3',4'-epoxycyclohexyl)-8,9-epoxy-2,4-dioxaspiro[5.5]undecane, the 3',4'-epoxycyclohexylmethyl ester of 3,4-epoxycyclohexanecarboxylic acid, butadiene diepoxide or isoprene diepoxide, epoxidized linoleic derivatives or epoxidized polybutadiene.

Preferred epoxy resins are diglycidyl ethers or advanced diglycidyl ethers of dihydric phenols or dihydric aliphatic alcohols of 2 to 4 carbon atoms, preferably the diglycidyl ethers or advanced diglycidyl ethers of 2,2-bis(4-hydroxyphenyl)propane and bis(4-hydroxyphenyl)methane or a mixture of these epoxy resins.

Although compositions containing a resin component consisting only of epoxy resins constitute an important embodiment of the invention, the curable compositions may also contain polyisocyanates in addition to the epoxy resins.

Suitable polyisocyanates are all polyisocyanates which are crosslinkable, including hexamethylene diisocyanate (HDI), trimethylhexamethylene diisocyanate (TMDI), cyclohexane diisocyanate (CHDI), isophorone diisocyanate (3,5,5-trimethyl-1-isocyanato-3-isocyanatomethylcyclohexane; IPDI), methylenedicyclohexyl isocyanate (HMDI), p-phenylene diisocyanate (PPDI), diisocyanatotoluene (TDI), e.g. 2,4-diisocyanatotoluene, 2,6-diisocyanatotoluene and technical mixtures of both isomers, naphthylene diisocyanate (NDI), preferably 1,5-naphthylene diisocyanate, dianisidine diisocyanate (DADI), methylenediphenyl diisocyanate (MDI), preferably the 4,4'-isomer, and also technical mixtures of different isomers, for example 4,4'- and 2,4'-isomers, or polymethylenepolyphenyl isocyanates (PAPI). Also very suitable are polyisocyanates which are obtainable by reaction of polyisocyanates with themselves via isocyanato groups, such as uretdiones or carbodiimide compounds which are formed by reaction of two isocyanate groups, or isocyanurate or biuret compounds which are formed by reaction of three isocyanato groups. Also suitable for use in the practice of this invention are polyisocyanate prepolymers which contain on average more than one isocyanato group per molecule and are obtained by prereacting a molar excess of one of the polyisocyanates referred to above with an organic material that contains at least two active hydrogen atoms per molecule, typically in the form of hydroxyl groups as in polyalkylene glycols. Isocyanates such as those mentioned above are commonly available and commercially obtainable in profusion.

Preferred polyisocyanurates are methylenediphenyl diisocyanate (MDI), isophorone diisocyanate (IPDI), hexamethylene diisocyanate, diisocyanatotoluene (TDI), e.g. 2,4-diisocyanatotoluene, 2,6-diisocyanatotoluene and technical mixtures of both isomers, and prepolymers of the cited isocyanates with polyalcohols as well as reaction products which are obtainable by reaction of the polyisocyanates with themselves via isocyanato groups.

The free isocyanato groups of the polyisocyanates may also be blocked in conventional manner, conveniently with phenols, oximes, pyrazoles or indazoles. Pyrazole-blocked polyisocyanates are preferred, because they liberate isocyanate again even at relatively low temperatures from about 80° C. and begin to harden.

The preparation of pyrazole-blocked polyisocyanates is disclosed, inter alia, in US-A-4 976 837 and in EP-A-0 500 495. It can be carried out by quantitative reaction of suitable pyrazoles with the polyisocyanates under inert gas. The process is preferably carried out at elevated temperature and in a suitable inert solvent (e.g. toluene), without or with a catalyst (e.g. dibutyltin laurate). Cooling may be necessary because of the reaction of both compounds. The pyrazoles used for blocking preferably have the formula

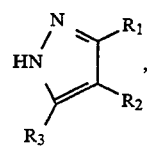

wherein $R_1$, $R_2$ and $R_3$ are each independently of one another hydrogen, hydroxyl, alkyl, preferably of 1 to 5 carbon atoms, alkoxy, alkylthio, preferably of 1 to 5 carbon atoms, methyl and methoxy again being especially preferred, aryl containing up to 10 ring carbon atoms, preferably phenyl, which may in turn carry substituents, typically $C_1$-$C_4$alkyl or $C_1$-$C_4$alkoxy; or arylalkyl, typically aryl($C_1$-$C_4$)alkyl, preferably arylmethyl, most preferably benzyl. Pyrazoles of this kind are commercially available or can be obtained by conventional methods, conveniently by reacting suitable i,i+2-diketones, typically a 1,3-diketone, with hydrazinc, with or without a solvent (e.g. toluene).

If mixtures of epoxy resins and polyisocyanates are used, then the amount of epoxy resin is preferably at least 50% by weight, even better at least 70% by weight, of the total resin component.

The compounds of formula 1 may be the sole hardener of the novel compositions. In this case they are used typically in an amount of 1 to 10% by weight, based on the epoxy resin or on the mixture of epoxy resins and polyisocyanates.

They may, however, also be used in the presence of other customary hardeners for epoxy resins, typically dicyandiamide or amine hardeners such as imidazole. In this case smaller amounts of the triazine compound will suffice and it will preferably be used in an amount of 0.1 to 5% by weight, also based on the epoxy resin or on the mixture of epoxy resins and polyisocyanates.

A preferred embodiment of the novel compositions comprises dicyandiamide as further hardener component, conveniently in an amount of 5 to 10% by weight, based on the resin. Although compositions of this kind have good bond strength and storage stability, they are not so weakly reactive as the corresponding compositions containing dicyandiamide as sole hardener. The compounds of formula 1, which are present in these compositions in an amount of 0.5 to 2.5% by weight, based on the epoxy resin, act as reaction accelerators.

In addition to the cited components, the novel compositions may contain customary additional components in the amounts conventionally used, including viscosity regulators, extenders, fillers, reinforcing agents, metal particles, pigments, dyes, plasticisers, adhesion promoters, fungicides, antioxidants, flow control agents, diluents, including reactive diluents such as epoxy resins, and other similar components.

The novel curable compositions can be used quite generally for making cured products and can be used in a formulation adapted to suit each specific end use as coating compounds, paints and varnishes, compression moulding materials, dipping resins, casting resins, impregnating resins, laminating resins, one- or two-component adhesives or matrix resins. They may be suitably used for making prepregs, composites, moulded articles of all kinds or for encapsualting electrical or electronic components. A particular utility of the compositions based on mixtures of epoxy resins and polyisocyanates is the fabrication of cured products into which modifiers such as plasticisers or flexibilisers have been incorporated, the polisocyanate component constituting the modifier for the epoxy resin component (interpenetrating polymer networks).

Particularly preferred utilities are those for which it is desired to achieve a high bond strength of the novel cured material, i.e. the use of the novel compositions as adhesives, coating compounds or for making prepregs.

Particularly suitable compositions for these utilities are those containing compounds of formula 1, wherein $R_1$ to $R_9$ are hydrogen, alkyl or aryl.

The novel compositions can be rapidly cured at relatively low temperatures. The cure temperature will generally be in the range from 20° to 200° C., preferably from 60° to 180° C. and, most preferably, from 80° to 120° C. Curing can be effected by applying heat in any form. The cure can be conveniently effected with microwaves or by induction heating, in which latter case the compositions must of course contain electrically conductive particles, typically metal particles.

A particular advantage of the novel compositions is, however, that they can be cured even at quite low temperature in the range below 120° C., preferably below 110° C., at a rate that suffices for practice. The gel times of the compositions are less than 30 minutes even in the temperature range of 100° to 120° C. The invention therefore also relates to a process for thermally curing epoxy resins or mixtures of epoxy resins and polyisocyanates, which comprises using a compound of formula 1 as sole hardener or in conjunction with dicyandiamide as second hardener and carrying out the cure in the temperature range below 120° C. The cure is normally carried out with simultaneous shaping to moulded articles, impregnations, coatings or bonds.

The products obtained from the compositions of this invention by thermal curing are distinguished in particular by a high $T_G$ value and superior temperature resistance. The invention thus further relates to the products obtained by thermal cure of the novel compositions.

The following Examples illustrate the invention in more detail.

EXAMPLE 1

Into a 3 liter round flask equipped with reflux condenser, nitrogen inlet, dropping funnel, thermometer and mechanical stirrer are placed 5.28 mol of imidazole (10% excess) in 1.2 liters of dry tetrahydrofuran. With good stirring, a solution of 0.8 mol of cyanuric chloride in 0.8 liter of tetrahydrofuran is slowly added dropwise. The suspension which forms in the course of the exothermic reaction is refluxed for 3 hours, then cooled to room temperature and filtered. The filter residue is washed with cold water. With good stirring, the filtrate is added dropwise to 4 liters of cold water. After filtration, the filter residue is also washed with cold water and the combined residues are dried to constant weight at 60° C. under high vacuum, giving pure tris(imidazol-1-yl)triazine of m.p. 260° C. in 93% yield.

Elemental analysis: calcd C 51.61% H 3.25% N 45.14% found C 51.72% It 3.32% N 45.16%

$^1$H-NMR($\delta$[ppm]in CDCl$_3$): 8.7(s); 7.9(t, J=1.4Hz); 7.3(t, J=1.4Hz) The aqueous solutions contain virtually pure imidazolium hydrochloride, which can be isolated by concentration.

EXAMPLE 2

Into a 1 liter round flask equipped with reflux condenser, nitrogen inlet, dropping funnel, thermometer and mechanical stirrer are placed 0.9 mol of imidazole and 0.945 mol of triethylamine (5% excess) in 0.4 liter of dry tetrahydrofuran. With good stirring, a solution of 0.3 mol of cyanuric chloride in 0.4 liter of tetrahydrofuran is slowly added dropwise. The suspension which forms in the course of the exothermic reaction is refluxed for 3 hours, then cooled to room temperature and filtered. The filter residue is washed with cold water.

With vigorous stirring, the filtrate is added dropwise to 1.2 liters of cold water. After filtration, the filter residue is also washed with cold water and the combined residues are dried to constant weight at 60° C. under high vacuum, giving tris(imidazol-1-yl)triazine in 89% yield in a purity matching that of the product obtainable in Example 1.

EXAMPLE 3

The procedure of Example 1 is repeated, but replacing imidazole with 2-methylimidazole, to give tris(2-methylimidazol-1-yl)triazine in 78% yield. When carrying out the procedure of Example 2, the same product is obtained in 75% yield.

Melting point: 266° C.

Elemental analysis: calcd C 56.07% H 4.71% N 39.23% found C 55.48% H 4.70% N 39.34%

EXAMPLE 4

The procedure of Example 1 is repeated, but replacing imidazole with 2-ethyl-4-methylimidazole, to give tris(2-ethyl-4-methylimidazol-1-yl)triazine. When carrying out the procedure of Example 2, the product is obtained in similar yield.

Melting point: 187° C.

Elemental analysis: calcd C 62.20% H 6.71% N 31.09% found C 62.14% H 6.79% N 31.35%

$^1$H-NMR($\delta$[ppm]in CDCl$_3$): 7.51(q, J=1.1Hz); 3.31(q, J=7.4Hz); 2.27(d, J=1.1Hz); 1.46(t, J=7.4Hz).

EXAMPLE 5

The procedure of Example 2 is repeated, but replacing imidazole with 2-phenylimidazole, to give tris(2-phenylimidazol-1-yl)triazine in 59% yield.

EXAMPLE 6

The procedure of Example 1 is repeated, but replacing imidazole with 2-phenylimidazole, to give tris(2-phenylimidazol-1-yl)triazine in 84% yield.

Melting point: 193° C.

Elemental analysis: calcd C 70.99% H 4.17% N 24.84% found C 70.24% H 4.60% N 24.22%

$^1$H-NMR($\delta$[ppm]in DMSO-d$_6$): 7.59-7.47(m, 15H); 7.06(d, J=1.4Hz, 3H); 6.64(d, J=1.4Hz, 3H).

EXAMPLES 7-14

The finely pulverised hardener of each of the Examples listed in Table 1 is blended with an epoxy resin based on bisphenol A (epoxide equivalent 185-190 g/eq; viscosity (at 25° C. according to DIN 53 015): 10 000-12 000 mPa.s; Araldit®GY-250) and, where indicated, the Co hardener listed in Table 1, and passed twice over a 3 roll mill. The formulations have the properties stated in Table 1.

EXAMPLES 15-19

The procedures described in Examples 7-14 are carded out, but using hybrid systems based on epoxy resins and the following polyisocyanates in which all free isocyanato groups are blocked.

PIC 1=Prepolymer obtained by reacting 22.58% by weight of methylenediphenyl diisocyanate (Isonate®M 125 [DOW]), 67.72% by weight of a linear polyether polyol based on polypropylene glycol (Desmophen®1900 U [BAYER]) and blocked with 7.73% by weight of 3,5-dimethylpyrazole and 1.52% by weight of imidazole in the presence of 0.45% by weight of dibutyltin dilaurate (10% in xylene).

PIC 2=Prepolymer obtained by reacting 30.9% by weight of methylenediphenyl diisocyanate (Isonate®M 125 [DOW]), 47.0% by weight of a linear polyether polyol based on polypropylene glycol (Desmophen®1900 U [BAYER]) and blocked with 18.0% by weight of 3,5-dimethylpyrazole (4.1% by weight of dibutyltin dilaurate; 10% in xylene).

PIC3=Prepolymer obtained by reacting 9.92% by weight of toluene diisocyanate, 86.47% by weight of a polytetrahydrofuran with a molecular weight of c. 2000 and blocked with 2.65% by weight of 3,5-dimethylpyrazole (0.96% by weight of dibutyltin dilaurate).

The mixtures have the properties indicated in Table 2.

In Table 2:

epoxy resin 1 is the epoxy resin of Examples 7 to 14 epoxy resin 2 is a modified epoxy resin based on bisphenol A (Araldit®AY-103)

epoxy resin 3 is a mixture of a modified epoxy resin based on bisphenol A and 1,4-butanediol diglycidyl ether (Araldit®AW-2104)

epoxy resin 4 is an epoxy resin based on butanediol (Araldit®DY-026)

In Tables 1 and 2 the values for tensile shear strength relate to a full cure (60 minute cure at 160° C.). Stability is indicated in the Tables by the time taken until the viscosity at the given temperature has doubled.

TABLE 1

| Example | Hardener of Example (% by wt.) | Co-hardener (% by wt.) | Exothermic reaction[2] (max.) | ΔH [J/g] | $T_g$ [°C.] | Stability RT[3] | Stability 40° C. | Tensile shear strength (Al/Al) ISO 4587 | Gel time[4] at 100° C. | 120° C. | 140° C. | 160° C. |
|---|---|---|---|---|---|---|---|---|---|---|---|---|
| 7 | 4 (3.8) | — | 162 | 302 | 171 | 3 w[5] | 4 d[6] | 11.7 | 32' | 13' | 7' | 2'50" |
| 8 | 4 (1.9) | — | 158 | 145 | — | 6 w | — | 12.4 | 40' | 18' | 9.5' | 5'50" |
| 9 | 4 (7.6) | — | 162 | 435 | 151 | 3 w | — | 12.6 | 32' | 13' | 6' | 2'30" |
| 10 | 3 (3) | — | 149 | 313 | — | 2 w | — | 11.9 | 22' | 9' | 4' | 1'40" |
| 11 | 3 (2.6) | — | 146 | 434 | — | 1 w | — | 10.1 | 21' | 7.5' | 3.5' | 1'40" |
| 12 | 4 (0.5) | DICY[1] (5) | 160 | 253 | — | >8 w | 10 d | 15.5 | >60' | 30' | 10' | 3' |
| 13 | 4 (1) | DICY (5) | 156 | 296 | — | >8 w | 8 d | 14.6 | >60' | 16' | 7' | 2'30" |
| 14 | 4 (2) | DICY (10) | 155 | 417 | ~130 | >8 w | 7 d | 18 | 47' | 16' | 5' | 1'30" |

[1]dicyandiamide
[2]measured by DSC at a heating up rate of 10° C./minute
[3]room temperature
[4]' = min, " = s
[5]weeks
[6]days

TABLE 2

| Example | Formulation (amount in grams) | Exothermic reaction[2] (max.) | ΔH [J/g] | $T_g$ [20 C.] | Stability RT[3] | Stability 40° C. | Tensile shear strength (Al/Al) ISO 4587 | Gel time at[4] 100° C. | 120° C. | 140° C. | 160° C. |
|---|---|---|---|---|---|---|---|---|---|---|---|
| 15 | epoxy resin 1 (70) PIC1 (25) hardener of Ex. 4 (2) DICY[1] (5) | 167 | 374 | 142 | — | 10 d[6] | 9.6 | >60' | 26' | 9.5' | 2.7' |
| 16 | epoxy resin 2 (68.6) PIC1 (24.5) hardener of Ex. 4 (2) DICY (4.9) | 170 | 301 | 112 | >6 w[5] | 7 d | 3.5 | >60' | 35' | 11.5' | 2.5' |
| 17 | epoxy resin 3 (68.6) PIC1 (24.5) hardener of Ex. 4 (2) DICY (4.9) | 158 | 352 | — | >6 w | 10 d | 17.8 | >60' | 20' | 5.2' | 1.7' |
| 18 | epoxy resin 1 (58) epoxy resin 4 (14.5) PIC3 (21.7) hardner of Ex. 4 (1.5) DICY (4.3) | 159 | 422 | — | >6 w | — | 8.4 | 41' | 30' | 6' | 2' |
| 19 | epoxy resin 1 (58) epoxy resin 4 (14.5) PIC3 (21.7) hardener of Ex. 4 (1.5) DICY (4.3) | 172 | 448 | 108 | >6 w | 14 d | 50.4 | >60' | 29' | 14' | 1.7' |

[1,2,3,4,5,6]q.v. Table 1

What is claimed is:

1. A curable composition based on epoxy resins or a mixture of epoxy resins and polyisocyanates, at least 50% by weight of the total resin component of said mixture being epoxy resins and containing at least one compound of formula 1:

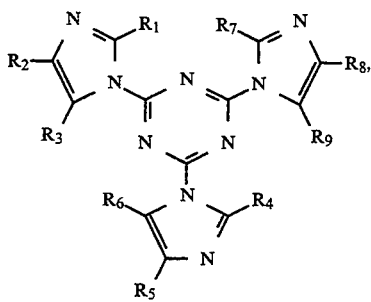

wherein [$R_1$, $R_2$, $R_3$, $R_4$, $R_5$, $R_6$, $R_7$, $R_8$ and $R_9$] $R_1$ to $R_9$ are each independently of one another hydrogen, $C_1$–$C_{10}$ alkyl which is unsubstituted or substituted by hydroxyl, halogen or $C_1$–$C_4$ alkoxy; $C_5$–$C_{10}$ aryl which is unsubstituted or substituted by halogen, $C_1$–$C_4$ alkyl or $C_1$–$C_4$ alkoxy; $C_5$–$C_{10}$aryl($C_1$–$C_4$)alkyl; or halogen, and $R_2$ together with $R_3$ or $R_5$ together with $R_6$ or $R_8$ together with $R_9$ optionally also each represent a fused benzene ring with the proviso that tris (benzimidazol-1-yl) triazine is excluded.

2. A composition according to claim 1, which contains one or more than one compound of formula 1, wherein $R_1$ to $R_9$ are each independently of one another hydrogen, $C_1$–$C_{10}$ alkyl, [preferably $C_1$–$C_4$alkyl,] or $C_5$–$C_5$–$C_{10}$ aryl.

3. A composition according to claim 2, which contains one or more than one compound of formula 1, wherein $R_1$ to $R_9$ are each independently of one another $C_1$–$C_4$ alkyl or phenyl.

4. A composition according to claim 1, which contains one or more than one compound of formula 1, wherein $R_1$, $R_4$ and $R_7$ are each identical and/or, $R_2$, $R_5$ and $R_8$ are each identical and/or $R_3$, $R_6$ and $R_9$ are each identical, but excluding tris(benzimidazol-1-yl)triazine.

5. A composition according to claim 1, which contains a resin component consisting only of epoxy resins.

6. A composition according to claim 1, which contains pyrazole-blocked polyisocyanates.

7. A composition according to claim 1, which contains the compound of formula 1 in an amount of 1 to 10% by weight, based on the epoxy resin, or, if a polyisocyanate is present, on the mixture of epoxy resin and polyisocyanate.

8. A composition according to claim 1, which contains an additional hardener and the compound of formula 1 in an amount of 0.1 to 5% by weight, based on the epoxy resin, or, if a polyisocyanate is present, on the mixture of epoxy resin and polyisocyanate.

9. A composition according to claim 8, which contains dicyandiamide as additional hardener.

10. A cured product obtained by thermally curing a composition as claimed in claim 1.

11. A process for thermally curing epoxy resins or a mixture of epoxy resins and polyisocyanates, at least 50% by weight of the total resin component of said mixture being epoxy resins, which comprises using at least one compound of formula 1:

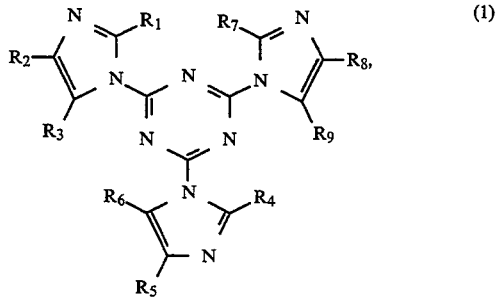

wherein [$R_1$, $R_2$, $R_3$, $R_4$, $R_5$, $R_6$, $R_7$, $R_8$ and $R_9$] $R_1$ to $R_9$ are each independently of one another hydrogen, $C_1$–$C_{10}$ alkyl which is unsubstituted or substituted by hydroxyl, halogen or $C_1$–$C_4$ alkoxy; $C_5$–$C_{10}$ aryl which is unsubstituted or substituted by halogen, $C_1$–$C_4$ alkyl or $C_1$–$C_4$ alkoxy; $C_5$–$C_{10}$aryl($C_1$–$C_4$)alkyl; or halogen, and $R_2$ together with $R_3$ or $R_5$ together with $R_6$ or $R_5$ together with $R_9$ optionally also each represent a fused benzene ring, with the proviso that tris (benzimidazol-1-yl) triazine is excluded, either as sole hardener or in conjunction with dicyandiamide as second hardener, and carrying out the cure at a temperature below 120° C.

* * * * *